US005128053A

United States Patent [19]

Gummo et al.

[11] Patent Number: 5,128,053

[45] Date of Patent: Jul. 7, 1992

[54] COMPOSITION AND PROCESS FOR TREATING FABRICS IN CLOTHES DRYERS

[75] Inventors: Gene A. Gummo, Delaware; Gary W. Earl, Columbus; Nancy Johnston, Powell, all of Ohio

[73] Assignee: Sherex Chemical Company, Inc., Dublin, Ohio

[21] Appl. No.: 651,577

[22] Filed: Feb. 6, 1991

[51] Int. Cl.$^5$ .................. D06M 10/08; C07D 405/00; C07D 295/00

[52] U.S. Cl. ...................................... 252/8.6; 252/8.7; 252/8.75; 252/8.8; 252/8.9; 544/374; 544/386; 544/399; 544/400

[58] Field of Search ........................ 252/8.6, 8.7, 8.75, 252/8.8 R, 8.9; 544/386, 399, 400, 374

[56] References Cited

U.S. PATENT DOCUMENTS

| | | | |
|---|---|---|---|
| 3,095,373 | 6/1963 | Blomfield | 252/8.8 |
| 3,442,692 | 5/1969 | Gaiser | 117/120 |
| 3,634,947 | 1/1972 | Furgal | 34/60 |
| 3,676,199 | 7/1972 | Hewitt et al. | 117/109 |
| 3,686,025 | 8/1972 | Morton | 117/140 R |
| 4,068,069 | 1/1978 | Kato et al. | 544/391 |
| 4,339,391 | 7/1982 | Hofmann et al. | 260/401 |
| 4,459,400 | 7/1984 | Kuhfuss et al. | 528/302 |
| 4,767,547 | 8/1988 | Straathof et al. | 252/8.8 |

FOREIGN PATENT DOCUMENTS 1071298 6/1967 United Kingdom .

*Primary Examiner*—A. Lionel Clingman
*Assistant Examiner*—William S. Parks
*Attorney, Agent, or Firm*—Scully, Scott, Murphy & Presser

[57] ABSTRACT

This invention relates to compositions for use in automatic laundry dryers comprising at least one piperazine compound of the formula:

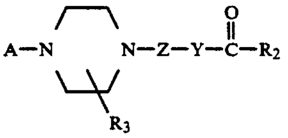

or

-continued

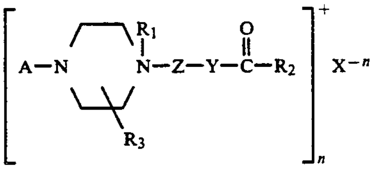

wherein
A is

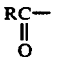

or

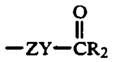

Y is —O— or —$NR_4$—;
Z is alkylene containing 2 to 6 carbon atoms in the principal chain and a total of up to 8 carbon atoms;
R is alkyl containing from about 8 to about 30 carbon atoms and may contain at least one of —S—, —O—,

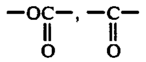

$CONR_4$, epoxy and double bond in the chain;
$R_2$ is alkyl containing up to about 30 carbon atoms and may contain at least one of —S—, —O—,

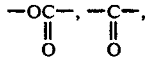

—$CONR_4$—, epoxy and double bond in the chain; and
$R_3$ and $R_4$ are each H or lower alkyl;
with the proviso that the total number of carbon atoms in the acyl R and $R_2$ groups is at least 18;
X is a salt-forming anion; $R_1$ is H, lower alkyl, hydroxy-lower- alkyl or benzyl; and n is an integer from 1 to 4.

22 Claims, No Drawings

COMPOSITION AND PROCESS FOR TREATING FABRICS IN CLOTHES DRYERS

The present invention relates to compositions and processes for treating textiles in an automatic laundry dryer to provide static control and softening.

BACKGROUND OF THE INVENTION

Fabrics can be treated to impart softness, static control and antistatic properties by addition of fabric softening compositions to the rinse cycle, as part of the detergent system, or in the automatic clothes drying cycle of the standard washing and drying routine. Treatment in clothes dryers has been shown to be an effective means for applying softening compositions to textiles. U.S. Pat. No. 3,441,692, to Gaiser, is one of the earlier examples of this softening mode in automatic clothes drying.

Various chemical compositions have been used commercially for softening fabrics when applied during the laundering operation. This softening or conditioning is normally understood and results in a smooth, fluffy feel to the touch. The most common softening compositions include one or more quaternary ammonium salts. Among the most commercially attractive are imadazoline salts, dimethyl dialkyl quaternary salts, and diamidoamine quaternary salts. The majority of these compounds are derived from fatty raw materials, and these cationics have been the subject of many innovations. See, for example, U.S. Pat. Nos. 3,634,947; 3,686,025; 3,095,373; 3,442,692. Disclosures specifically for dryer-added fabric softeners include U.S. Pat. No. 3,676,199. In all of the commercially used dryer-softener systems there is included from 10-30% of a release agent to accomplish the transfer of the active softener to the textile being dried. This requirement for the release agent results in additional handling and manufacturing costs.

We have found that certain salts based on piperazine provide surprisingly good softening and antistatic properties while exhibiting excellent transfer from the dryer sheet to the clothes in the automatic clothes dryer.

It is, therefore, an object of the present invention to provide a material for the treatment of textiles in an automatic dryer to provide softness and static control to the fabric with improved transfer properties from the dryer sheet to the clothes.

It is an additional objective of the present invention to provide a softening system for use in an automatic laundry dryer comprising a softener exhibiting faster biodegradation than currently available systems.

It is an object of the present invention to provide a softening sytem for use in an automatic laundry dryer which requires less or no additive for satisfactory release from the substrate.

SUMMARY OF THE INVENTION

The present invention relates to an article of manufacture adapted for use to provide softening and antistatic properties to fabrics when dried in an automatic laundry dryer comprising amines of structure I and salts thereof:

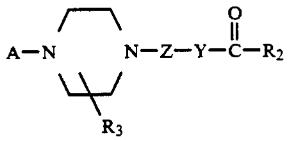

I wherein A is

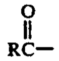

or

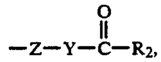

Y is O or $NR_4$; R is 8-30 alkyl or 8-30 alkyl containing at least one of —S—, —O—,

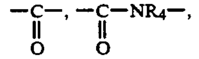

epoxy group and double bond in the chain; each $R_2$ is 1-30 alkyl or 8-30 alkyl containing at least one of —S—, —O—,

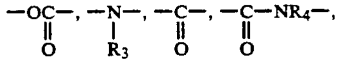

double bond, and epoxy group in the chain with the proviso that the total number of carbon atoms in the acyl R groups (i.e., R and $R_2$) is at least 18, and preferably above 30, $R_3$ and $R_4$ are each H or lower alkyl; and Z is alkylene containing 2-6 carbon atoms in the principal chain and up to a total of 8 carbons and salts thereof, including acid addition salts (HX) and quaternary ($R_1X$) salts, where $R_1$ is lower alkyl, hydroxy lower alkyl or benzyl and X is a salt forming anion.

Compositions of this invention can be disposed in any manner into an automatic dryer under conditions which provide for release for an effective amount of the composition on the fabrics. Normally, softening compositions are deposited on an absorbant substrate as an impregnate or as a coating.

These compositions, in addition, can contain soil release components for providing soil release benefits, and may comprise optional cationic and/or nonionic softening agents.

DESCRIPTION OF THE INVENTION

The fabric conditioning composition of the present invention comprises amines of structure I and salts thereof:

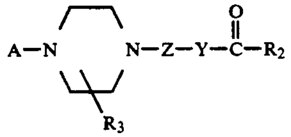

I wherein A is

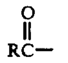

or

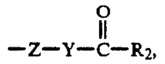

Y is O or $NR_4$; R is 8-30 alkyl or 8-30 alkyl containing at least one of —S—, —O—,

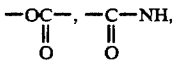

epoxy group and double bond in the chain; each $R_2$ is 1-30 alkyl or 8—30 alkyl containing at least one of —S—, —O—,

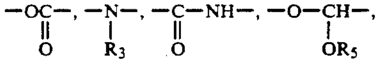

double bond, and epoxy group in the chain with the proviso that the total number of carbon atoms in the acyl R groups (i.e., R and $R_2$) is at least 18, and preferably above 30, $R_3$ and $R_4$ are each H or lower alkyl; and Z is alkylene containing 2-6 carbon atoms in the principal chain and up to a total of 8 carbons and salts thereof, including acid addition salts (HX) and quaternary ($R_1X$) salts, where $R_1$ is lower alkyl, hydroxy lower alkyl or benzyl and X is a salt forming anion.

Compounds of this invention are readily prepared by known procedures. The present products are prepared from

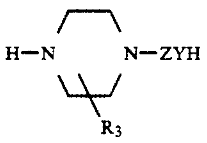

and

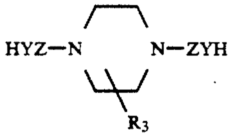

wherein Z and Y have the same meaning as previously described, by reaction of suitable acids of the formula $RCO_2H$ and $R_2CO_2H$ or acylating derivatives thereof. Thus, there can be prepared compounds of the following formulae:

TABLE II

| | Structure |
|---|---|
| 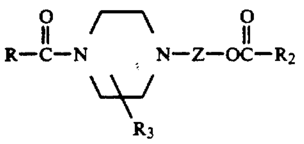 | Ia |
| 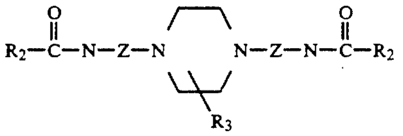 | Ib |
| 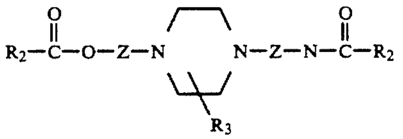 | Ic |
| 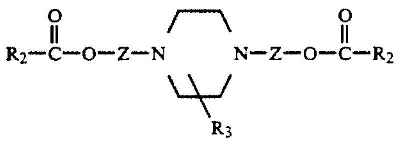 | Id |
| 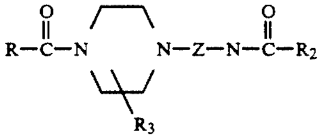 | Ie |

Compounds of Structure Ia where R and $R_2$ are the same are prepared by reaction of two moles of acid, or acylating derivatives thereof, of the formula $RCO_2H$ with N-hydroxyalkylpiperazine; where R and $R_2$ differ, the compound is prepared by reaction of an acid, or acylating derivatives thereof, of formula $R_2CO_2H$ with a piperazine of the formula:

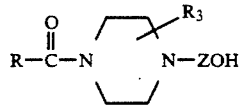

which latter compound can be prepared by acylation of the N-hydroxyalkylpiperazine with an acid or acylating derivative of the formula $RCO_2H$, under conditions which inhibit ester formation.

Compounds of Structure Ib are prepared by reaction of N, N bis(aminoalkyl) piperazine with acid or acylating derivatives thereof of the formula $R_2CO_2H$ under amide-forming conditions; where the two $R_2$ groups of the compound are the same, two equivalents of the acylating agent are used. Where the $R_2$'s differ, stepwise amidation should be used.

Compounds of Structure Ic where the $R_2$'s are the same are prepared by reacting N-hydroxyalkyl N'-aminoalkylpiperazine with two equivalents of the acylating agent employed. Where the $R_2$'s differ, the acylating proceeds stepwise with one equivalent of acylating agent forming the amide, and the second equivalent forming the ester.

Compounds of Structure Id are prepared by a similar procedure as described for Ib, but employing N,N-bis(-hydroxyalkyl)piperazine as the starting material.

Compounds of Structure Ie are prepared by a similar procedure as described for Ia, but employing the aminoethylpiperazine as the starting material.

The salts of the compounds of this invention are prepared by standard procedures, i.e., by reaction of the tertiary amine with HX or $R_1X$ in which X is a salt-forming anion and $R_1$ is loweralkyl, hydroxyloweralkyl or benzyl. X can be sulfate, ethylsulfate, carbonate, borate, phosphate, halide, carboxylate and the like. Preferred anions are chloride and methyl sulfate.

Preferred compounds include compounds of Structure Ia, Id and Ie, and salts thereof, particularly those wherein R and $R_2$ are long chain alkyls of $C_{12-22}$, Z is $—(CH_2)_2—$ and $R_3$ is H, which are readily prepared by quaternization of the aforesaid tertiary amine with diethyl sulfate, dimethyl sulfate or methyl chloride or, alternatively, by reaction with a dialkylcarbonate, i.e., dimethylcarbonate, followed by reaction with a suitable acid, such as phosphoric, sulfuric, lower alkanoic acid or hydroxylower- alkanoic acid, e.g., lactic acid. Most preferred are compounds of Structure Ia.

The acids or derivatives used for acylation to amide or ester groups include alkanoic acids from $C_2$ through $C_{22}$, saturated or unsaturated, substituted or unsubstituted.

Especially suitable are fatty acids derived from naturally-occurring animal and vegetable or fish oils. The acids can readily be obtained by hydrolysis of the naturally-occurring triglycerides. The acids can be converted to their acylating derivatives by halogenation to acyl halides, or by esterification/transesterification to the lower alkyl, e.g., methyl, esters, or by anhydride formation, including anhydrides formed with lower alkanoic acids such as acetic acid. The acids or their acylating derivatives can be used with retention of the unsaturation found in the natural products or the unsaturation can be reduced or eliminated entirely by hydrogenation. Hydroxy substituted fatty acid can be obtained from castor oil, i.e., 12-hydroxyoleic acid. Unsaturated acids such as oleic (cis octadecenoic acid) can be epoxidized to epoxystearic acid by use of peroxides or peracids.

The following examples further illustrate the present invention.

PREPARATION OF THE ESTER AMIDE

Two moles of the desired fatty acid were placed in a 2-liter 4-neck flask. The flask was fitted with an addition funnel, air condenser, thermometer, and mechanical stirrer. The flask was heated until the acid was melted and then 1 mole (150g) of 1-(2-hydroxyethyl) piperazine was added dropwise via the addition funnel. Immediately upon addition, the solution turned dark brown. After addition was complete, the flask was heated to 150°-170° C. and the reaction was monitored by change in acid value. Periodically, the reaction was submitted to a water aspirated vacuum to remove water from the system. A typical preparation usually took between 8 and 12 hours. After completion of the reaction, the hot molten material was poured into two separate 1-liter Erlenmeyer flasks and allowed to cool to room temperature.

After cooling, the material solidified. The solid material was dissolved in methylene chloride (or toluene) and $MgSO_4$ was added to the organic solution to remove any remaining water. The solution was filtered and the organic solvent removed in vacuo. The residual solid was recrystallized from ethyl acetate. Acid values ranged from 2-6 (theoretical 0.0). Total amine values (TAV) ranged from 95-110 for the myristic acid derivative (theoretical 84.7). IR data showed two carbonyl bands at 1735 $cm^{-1}$ (ester carbonyl) and 1655 $cm^{-1}$ (amide carbonyl). No amine or hydroxyl bands were found. C-13 NMR confirmed the desired structure.

QUATERNIZATION OF ESTER AMIDE

The ester amide of 1-(2-hydroxyethyl) piperazine, 0.578 mole, 370 ml of isopropyl alcohol, and 64 g of $NaHCO_3$ was placed in a 2-liter Parr reactor. The reactor was sealed and methyl chloride was charged into the reactor while stirring until the temperature and pressure stabilized (usually at 30° C. and 50 psi). The reactor was heated to 100° C. and the reaction was monitored by TAV. Reaction times were normally between 6 and 8 hours. After the reaction was complete, the reactor was cooled to 80° C. and vented. The resulting mixture was vacuum filtered and the resulting filtrate was evaporated to dryness. Typical yields ranged from 95-100% for the myristic acid derivative and 91-93% for the stearic acid derivative. Wet analysis is shown in Table I.

TABLE I

Analytical Results of Quaternization of Hydroxyethyl Piperazine Ester Amide

| | C14 Esteramide | C18 Esteramide |
|---|---|---|
| % FA | 1.8% | 2.3% |
| % AHH | 1.8% | 0.0% |
| % Quat | 99.1% | 83% (15% IPA) |

FA = fatty acid
AHH = amine hydrohalide
Quat = quaternary salt

IR data showed both carbonyl peaks present (1730 and 1645 $cm^{-1}$) $C^{13}$ NMR data shows new peak at 48.56 ($CH_3$ —N) and thus confirmed the structure. Chemical shifts of the other carbons were consistent with quaternary formation.

BIODEGRADATION

The compounds of this invention exhibit surprisingly rapid biodegradation. The compound of Formula I where Z is 2; Y is 0; R and $R_2$ are $C_{17}$ alkyl chains derived from hardened tallow; $R_3$ is H; converted to its quaternary salt with $R_1X$ where $R_1$ is methyl; and X is Cl-(Structure II); and Structure II where R and $R_2$ each are $C_{13}$ instead of tallow (Structure IIa) was evaluated for biodegradation according to the following scheme:

The comparative quaternary salts evaluated were di(hydrogenated tallow) dimethylammonium chloride (Adogen® 442, Structure III); ditallow dimethylammonium chloride (Adogen® 470, Structure IV); distearyl dimethyl ammonium chloride (Arosurf® TA 100, Structure V); methyl, tallowamidoethyl, 2-tallowimidazolinium methyl sulfate (Varisoft® 475, Structure VI); methyl, bis (tallowamidoethyl), 2-hydroxy ethyl ammonium methylsulfate (Varisoft® 222, Structure VII); lauryltrimethyl ammonium chloride (Structure VIII), all of which are listed in Table III.

All compounds were obtained from Sherex Chemical Co. (Dublin, Ohio). The compounds with trade names in parentheses were used as supplied; the others were purified by recrystallization from appropriate solvents. The bacteria were obtained as Polyseed (Polybac Corp.). Polyseed is a mixture of 12 bacteria which are characteristic of those found in wastewater and POTW. HPLC grade water was used (Fisher) and dissolved oxygen was measured with a dissolved oxygen probe and meter (Yellow Springs Instruments, Model 58).

Biodegradation samples were incubated at 20±0.3° C. in the dark.

ACCLIMATION OF BACTERIA

A capsule containing Polyseed was dispersed into 250 ml dilution water where the oxygen level in the water was 15.0±0.2 mg/l. The water used was standard APHA dilution water as described in the Standard Methods. The nutrient solution was prepared from 25 g peptone, 15 g beef extract, 4 g urea, 4 g glucose, and 3 g $KH_2PO_4$ dissolved into 1000 ml HPLC grade water. Over a five day period, the bacteria were given less nutrient solution and more QAC solution until the bacteria were not receiving any nutrient solution. On the first day the bacteria were fed 1 ml of nutrient solution and 10 mg of QAC. On the second day 1 ml of nutrient solution and 20 mg QAC was added to the culture along with 20 mg of quaternary ammonium compound (QAC). On the fourth day of 0.5 ml of nutrient solution and 80 mg QAC was added. On the fifth day 0.2 ml nutrient solution was added, along with 100 mg QAC and 1 ml diammonium phosphate solution at a concentration of 24 g/l water. Fifty ml aliquots of HPLC water with a dissolved oxygen level of 15 mg/2/l were added to the cultures each day after the first day. After the five day period 2 ml aliquots of the bacteria were immediately used in closed bottle testing.

METHOD

The procedure used for biodegradation evaluation is a variation of the Closed Bottle or Biochemical Oxygen Demand (BOD) method. The method used is as described in Method 507 of the Standard Methods for the Examination of Waste and Wastewater; 15th ed., (1980) with the following exceptions: Classically the closed bottle test has been performed with activated sludge as the source of bacteria. We have chosen to use Polyseed to reduce the contribution of variable bacterial populations to experimental error. The bacterial composition is consistent within a lot of Polyseed and lot to lot variability was small. To eliminate any contribution to oxygen demand by organic materials in the water, HPLC grade water was used.

Acclimation of bacteria is one of the key factors in determining the biodegradability of QAC's. The bacteria used in each closed bottle test were acclimated over a five day period as noted above. When tests were repeated, new acclimated bacteria were prepared.

Each round of testing included a water control, a seed correction, a glucose/glutamic acid control, and a series of QAC's. All of the samples were incubated in the dark at 20° C. Dissolved oxygen measurements were taken periodically, typically every 5, 10, 15, 20, 25 and 28 days. Tests were considered invalid if any one of the controls failed; failure was indicated by: (1) The dissolved oxygen level in the water control changed more than 0.2 mg/l over a period of five days, or (2) the seed correction sample showed a depletion outside the range 0.6–1.0 mg/l over the same five-day period. Biochemical oxygen demand values were not calculated, rather calculations of % biodegradation were conducted using the ratios of biochemical oxygen depletion (mg $O_2$ depleted/mg sample) to calculated oxygen depletion (theoretical-based on empirical formula of primary molecule) or chemical oxygen depletion (experimental-based on elemental analysis).

Comparative data were obtained for ammonium quaternary salts using the same procedure and the results are shown in Table III based on the 20 day measurement.

These data show the surprising rapidity of the initial stages of biodegradation of the compounds of this invention when compared to other compounds having good softening properties. Although these and other compounds are presumed to ultimately degrade to completion, the compounds of this invention exhibit the unexpected and valuable characteristics of rapid early stage biodegradation.

TABLE III

| Structure | Structure | % Degraded (20 day test) | Softening Ability |
|---|---|---|---|
| 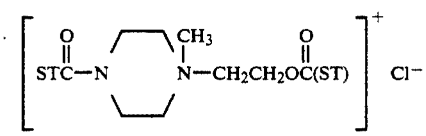 | II | 43 | Above average |
| 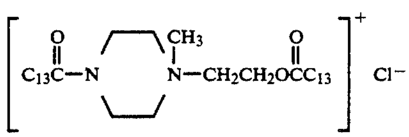 | IIa | 72 | Above average |
| 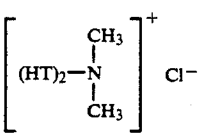 | III | 20 | Excellent |
| 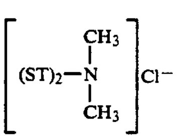 | IV | 38 | Excellent |

TABLE III-continued

| Structure | Structure | % Degraded (20 day test) | Softening Ability |
|---|---|---|---|
| 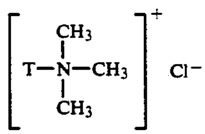 | V | 64 | Below average |
| [di T imidazoline]$^{+}$MeSO$_4^{-}$ | VI | 47 | Above average |
| 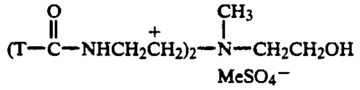 | VII | 48 | Average |
| 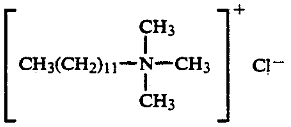 | VIII | 86 | Below average |

HT = hardened tallow acid residue
T = unhardened tallow acid residue
ST = stearic acid residue (91% $C_{18}$)

It can be seen from Table III that the compound of this invention compares favorably in biodegradation to competitive structures which have good softening performance.

The compounds of this invention show high utility in softening fabric in household or industrial washing routines. They can be dried and incorporated as powder in formulated detergents for use during the wash cycle; they can be added as a dispersion to the rinse cycle; or they can be supported on an inert fabric carrier for deposition during the drying operation, all by methods well known to the art. The physical characteristics of the compounds of this invention can be modified by selection of the fatty chains, and the substituents $R_1$ and $R_4$.

The compounds of this invention were evaluated for their softening ability according to the following procedures standardized by the Chemical Specialities Manufacturers Association (CSMA).

| Procedure | Designated Test |
|---|---|
| Fabric Treatment | DCC-13A |
| Softener Evaluation | DCC-13B |
| Static Control | DCC-F |

FORMULATION OF SOFTENER FOR EVALUATION

A 6% dispersion of Structure II in isopropyl alcohol (IPA) (76.4% solids, 23.6% IPA) was formulated into a rinse cycle softening system as follows:

| Ingredients | Net % |
|---|---|
| Structure II | 8.1 |
| Nonionic (Neodol 25-9) | 1.0 |
| 150 ppm $H_2O$ (160° F.) | 90.9 |

PROCEDURE

1. Add water to a tared beaker
2. Heat the water to 160° F.
3. Place beaker with water under a lab mixer and agitate at 500 RPM.
4. Add nonionic and allow to stir 1-2 minutes.
5. Add quat (Formula II) and allow dispersion to cool to room temperature (R/T). Continue agitation.
6. Stop agitation, place beaker on balance and add R/T dilution water until desired total weight.
7. Place beaker back under lab mixture and agitate dispersion 5-10 minutes longer.

Results of the softening evaluation according to DCC-13A and 13B were as follows based on the three days of testing using eight panelists per day (4 best, 1 worst) are shown in Table IV.

TABLE IV

| Formula | Day 1 | Day 2 | Day 3 | Average |
|---|---|---|---|---|
| III | 3.5 | 3.6 | 3.6 | 3.6 |
| II | 2.8 | 2.8 | 2.2 | 2.6 |
| VI | 2.3 | 2.4 | 2.3 | 2.3 |
| VII | 1.5 | 1.6 | 2.1 | 1.7 |

DIAMINE (Structure Ie)

The compound of this invention where Y is $NR_4$, R and $R_2$ and $C_{17}$ alkyl chains derived from hardened tallow; $R_3$ and $R_4$ are H; Z is ethylene, $R_1$ is methyl and; X is $MeSO_4$ Formula X

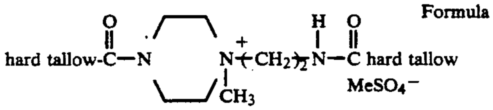

PREPARATION OF DIAMIDE

Two moles of fatty acid are weighed into a round bottom reaction flask. One mole of aminoethylpiperazine (AEP) is weighed into an addition funnel. A mechanical stirrer, thermometer, $N_2$ sparge tube, and a water trap are provided The fatty acid is melted at a temperature of 70°-80° C., under nitrogen blanket. When the acid is thoroughly melted, the mass is heated to 105°-100° C., and AEP is slowly added. An exotherm will raise the temperature approximately 10°-20° C.

When all the amine is added, raise the temperature to 165°-170° C. Maintain nitrogen sparge to remove water from the system. The reaction is followed by acid value determination. The reaction is considered complete when the acid value is ten or less.

PREPARATION OF METHYL SULFATE QUAT FORMULA X

One mole of the above diamide is weighed into a four neck round bottom flask. To that one mole, add enough IPA to make a 50% solids solution. The flask is equipped with a mechanical stirrer, thermometer, and condenser. To maintain a good color, 0.95 mole of dimethyl sulfate (DMS) is used; DMS is added via an addition funnel. Heat the diamide/IPA mixture to 80° C. When the temperature is reached, slowly add the DMS (exothermic). When the DMS is all added, heat for one hour. The reaction is followed by acid and amine values. The Formula X product was evaluated for softening according to CSMA procedure DCC-13 A&B against Adogen 442 (Formula III) and an unsoftened control.

TABLE V

| Softener | Panel 1 | Panel 2 | Average |
|---|---|---|---|
| Structure III | 3.6 | 3.9 | 3.8 |
| Structure X | 3.0 | 2.5 | 2.8 |
| Control | 1.3 | 1.0 | 1.2 |

Table VI describes compound types within the scope of this invention. ($R_3$ is H)

TABLE VI

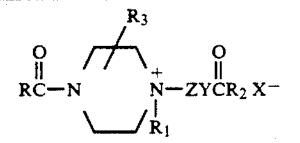

| R | $R_2$ | $R_1$ | $R_3$ | Z | Y | X | Structure |
|---|---|---|---|---|---|---|---|
| T | T | Me | — | $C_2H_4$ | O | $Cl^-$ | XI |
| T | T | Me | — | $C_3H_7$ | O | $A^-$ | XII |
| T | T | Me | — | $C_2H_4$ | O | lactate | XIII |
| T | T | Me | — | $C_2H_4$ | O | $MeSO_4^-$ | XIV |
| IS | IS | Me | — | $C_2H_4$ | O | $A^-$ | XV |
| T | T | Me | — | $C_2H_4$ | O | $AcO^-$ | XVI |
| CS | CS | Me | — | $C_2H_4$ | O | $A^-$ | XVII |
| EO | EO | Me | — | $C_2H_4$ | O | $A^-$ | XVIII |
| oleyl | oleyl | Me | — | $C_2H_4$ | O | $A^-$ | XIX |
| T | T | Me | Me | $C_2H_4$ | $NR_4$ | $Cl^-$ | XX |

T is tallow (hydrogenated or non-hydrogenated) acid chain ($C_{15}$-$C_{17}$).
IS is isostearic acid chain.
$X^-$ is any anion including $Cl^-$, $Br^-$, $MeSO_4^-$, $RCO_3^-$, $(R_3)_2PO_4^-$; $RCO_2^-$.
EO is epoxy oleyl.
CS is castor acids (12-hydroxyoleic).

EVALUATION AS DRYER-ADDED SOFTENER

Compounds of this invention have been found to be surprisingly effective as dryer softeners. Testing of structure IIb (Structure I where Z is 2; Y is 0; R and $R_2$ ar $C_{17}$ alkyl chains derived from hardened tallow; $R_3$ is H; converted to its quaternary salt with R1X where $R_1$ is methyl and X is $MeOSO_3^-$) was compared to dimethyl dihydrogenated tallow methyl sulfate (Varisoft 137, Sherex Chemical Company, Inc.) with and without additives. Structure 2 showed good release characteristics and good softening even when no additives were used.

The dryer sheets were prepared according to the following procedure:

MATERIALS NEEDED hot plate
stainless steel plate 9"×11"
thermometer
balance capable of 0.01 gram sensitivity
drawdown bar
uncoated substrate—rayon or polyester (this method is not suitable for foam substrate)

COATING PROCEDURE

Preparation

Allow the steel plate and drawdown bar to preheat for at least one hour on top of the hot plate. Choose a temperature that is 10° C. above the melting point of the dryer coating.

Preheat the drawdown bar on top of the steel plate.

1. Cut dryer substrate into 9"×11" pieces.
2. Weigh the uncoated substrate pieces to 0.01 gram.
3. Place the uncoated substrate piece on the steel plate.
4. Melt about 2 grams more dryer base than your desired coating weight in an aluminum weighing dish.
5. Very rapidly pour the melted dryer base in a thin stream all over the piece of substrate.
6. Spread the dryer base in two directions with the drawdown bar.
7. Allow the sheet to cool about 30 seconds.
8. Reweigh the coated substrate piece. Subtract uncoated weight to determine the amount of coating applied.

EVALUATION OF RATE OF RELEASE

1. Weigh the coated dryer sheet to ±0.5 grams before start of cycle.

2. Fabric bundle must be freshly washed and rinsed. Preferred rinse cycle water temperature is 95° F. or hotter.

3. Preheat automatic clothes dryer on "hot" or "cotton" cycle for 10 minutes.

4. Place wet fabric bundle in clothes dryer with the preweighed dryer cycle fabric softener sheet and dry for 5 minutes on "hot".

5. After 5 minutes, remove and weigh the softener substrate.

6. Replace the softener substrate in the dryer and repeat steps 5 and 6 for at least 45 minutes. Every 5 minutes the dryer is stopped and the fabric softener piece is removed and weighed.

Table VII shows the composition of 3 softener systems tested on spun bonded polyester (Reemay, Inc.) at a coat rate of 1.7 g. per sheet. Although softener A, which is a commercial fabric softener (tested without a release aid additive, which is normally used) releases less than 50% under the test conditions. The sheet was unhandleable as the coated sheet; the softener A was brittle and flaked off, making it unacceptable as a commercial softener. Surprisingly, composition B, the compound of this invention (Structure II) is adequately released without additives. This is important in ease of handling and expense.

TABLE VII

| | A | B | C |
|---|---|---|---|
| Varisoft 137 | 100% | | 70% |
| Structure II | | 100% | |

TABLE VII-continued

| | A | B | C |
|---|---|---|---|
| Additive (1) | | | 30% |

(1) stearic acid ester of polyethylene glycol

The release of softener A containing 30% additive (C in Table V) did release to a lower level. However, the softening performance of C was no better than the composition of this invention.

The softening and static control exhibited by compositions based on Structure II was found to be equivalent to commercial dryer softeners when evaluated by test panels.

We claim:

1. A composition for use in an automatic laundry dryer comprising a fabric softening effective amount of at least one compound of the formula:

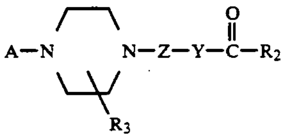

or

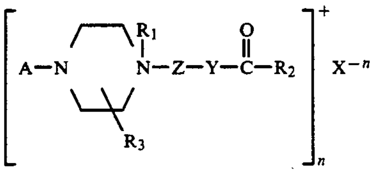

wherein

A is

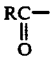

or

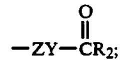

Y is —O— or —$NR_4$—;

Z is alkylene containing 2 to 6 carbon atoms in the principal chain and a total of up to 8 carbon atoms;

R is alkyl containing from about 8 to about 30 carbon atoms and may contain at least one of —S—, —O—,

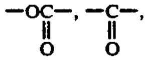

$CONR_4$, epoxy and double bond in the chain;

$R_2$ is alkyl containing up to about 30 carbon atoms and may contain at least one of —S—, —O—,

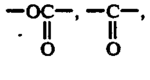

—$CONR_4$—, epoxy and double bond in the chain; and $R_3$ and $R_4$ are each H or lower alkyl;

with the proviso that the total number of carbon atoms in the acyl R and $R_2$ groups is at least 18;

X is a salt-forming anion;

$R_1$ is H, lower alkyl, hydroxyloweralkyl or benzyl; and n is an integer from 1 to 4.

2. A composition according to claim 1 wherein Y is —O—.

3. A composition according to claim 1 wherein X is chloride.

4. A composition according to claim 1 wherein X is alkyl carbonate.

5. A composition according to claim 1 wherein X is alkylsulfate.

6. A composition according to claim 1 wherein X is $R_3CO_3$—.

7. A composition according to claim 1 wherein R is alkyl containing from about 14 to about 22 carbon atoms.

8. A composition according to claim 1 wherein $R_2$ is alkyl containing from about 14 to about 22 carbon atoms.

9. A composition for use in an automatic laundry dryer comprising a fabric softening effective amount of at least one compound of the formula:

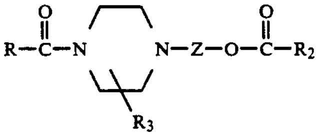

or

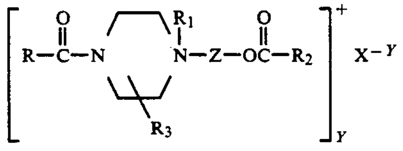

wherein

Z is alkylene containing 2 to 6 carbon atoms in the principal chain and a total of up to 8 carbon atoms;

R is alkyl containing from about 8 to about 30 carbon atoms and may contain at least one of —S—, —O—,

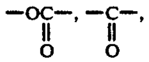

—$CONR_4$—, epoxy and double bond in the chain;

$R_2$ is alkyl containing up to about 30 carbon atoms and may contain at least one of —S—, —O—,

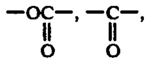

—$CONR_4$—, epoxy and double bond in the chain;

$R_3$ and $R_4$ are each H or lower alkyl;

with the proviso that the total number of carbon atoms in the acyl R and $R_2$ groups is at least 30;

X is a salt-forming anion;

$R_1$ is H, lower alkyl, hydroxyloweralkyl or benzyl; and

Y is an integer from 1 to 4.

10. A composition according to claim 9 wherein X is chloride.

11. A composition according to claim 9 wherein X is $R_3CO_3^-$.

12. A composition according to claim 9 wherein X is methylsulfate.

13. A composition according to claim 1 including dispensing means which provides for release of an effective amount of said compound at dryer operating temperatures.

14. A composition according to claim 13 wherein said dispensing means is a flexible substrate in sheet form having the said compound attached thereto in a weight ratio of said compound to dry substrate of from about 10:1 to about 0.25.

15. A composition according to claim 14 including soil release agents, and optionally cationic and nonionic fabric softeners and release aids.

16. A composition for use in a automatic dryer comprising a fabric softening effective amount of at least one compound of the formula:

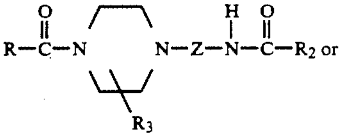

or

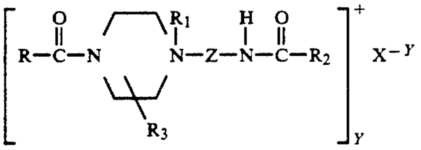

wherein

Z is alkylene containing 2 to 6 carbon atoms in the principal chain and a total of up to 8 carbon atoms;

R is alkyl containing from about 8 to about 30 carbon atoms and may contain at least one of —S—, —O—,

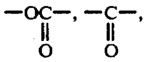

—$CONR_4$—, epoxy and double bond in the chain;

$R_2$ is alkyl containing up to about 30 carbon atoms and may contain at least one of —S—, 'O—,

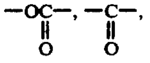

—$CONR_4$—, epoxy and double bond in the chain;

$R_3$ and $R_4$ are each H or lower alkyl;

with the proviso that the total number of carbon atoms in the acyl R and $R_2$ groups is at least 30;

X is a salt-forming anion;

$R_1$ is lower alkyl, hydroxyloweralkyl, or benzyl; and

Y is an integer from 1 to 4.

17. A composition for use in an automatic laundry dryer comprising a fabric softening amount of at least one compound of the formula:

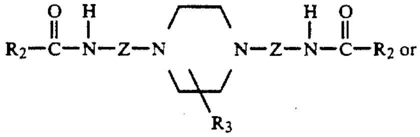

or

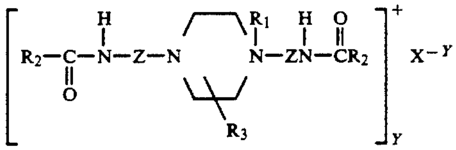

wherein

Z is alkylene containing 2 to 6 carbon atoms in the principal chain and a total of up to 8 carbon atoms;

$R_2$ is alkyl containing up to about 30 carbon atoms and may contain at least one of —S—, —O—,

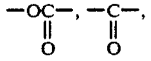

—$CONR_4$—, epoxy and double bond in the chain;

$R_3$ and $R_4$ are each H or lower alkyl;

with the proviso that the total number of carbons in the two acyl $R_2$ groups is at least 30;

X is a salt forming anion;

$R_1$ is H, lower alkyl, hydroxyloweralkyl or benzyl; and

Y is an integer from 1 to 4.

18. A composition for use in an automatic laundry dryer comprising at least one compound of the formula:

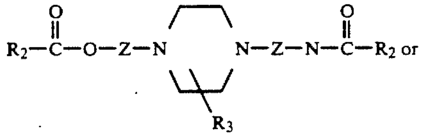

or

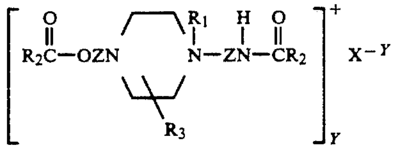

wherein

Z is alkylene containing 2 to 6 carbon atoms in the principal chain and a total of up to 8 carbon atoms;

$R_2$ is alkyl containing up to about 30 carbon atoms and may contain at least one of —S—, —O—,

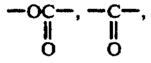

—$CONR_4$—, epoxy and double bond in the chain;

$R_3$ and $R_4$ are each H or lower alkyl;

with the proviso that the total number of carbons in the two acyl $R_2$ groups is at least 30;

X is a salt-forming anion;

$R_1$ is lower alkyl, hydroxyloweralkyl or benzyl; and

Y is an integer from 1 to 4.

19. A composition for use in an automatic laundry dryer comprising at least one compound of the formula:

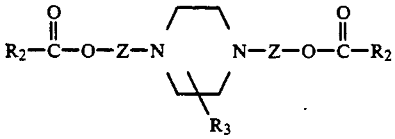

or

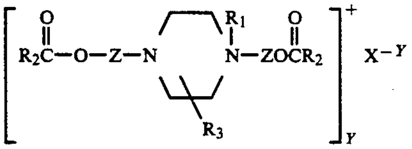

wherein

Z is alkylene containing 2 to 6 carbon atoms in the principal chain and a total of up to 8 carbon atoms;

$R_2$ is alkyl containing up to about 30 carbon atoms and may contain at least one of —S—, —O—,

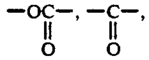

—$CONR_4$—, epoxy and double bond in the chain;

$R_3$ and $R_4$ are each H or lower alkyl;

with the proviso that the total number of carbons on the two acyl $R_2$ groups is at least 30;

X is a salt-forming anion;

$R_1$ is H, lower alkyl, hydroxyloweralkyl or benzyl; and

Y is an integer from 1 to 4.

20. A composition according to claim 17 wherein X is chloride.

21. A composition according to claim 17 wherein X is $R_3CO_3^-$.

22. A composition according to claim 17 wherein X is methylsulfate.

* * * * *